(12) United States Patent
Lim et al.

(10) Patent No.: US 9,572,748 B2
(45) Date of Patent: Feb. 21, 2017

(54) PRESCRIPTION CONTAINER AND SERVICE FOR MONITORING PATIENTS

(71) Applicant: Cellco Partnership, Basking Ridge, NJ (US)

(72) Inventors: Kevin Lim, Danville, CA (US); Alex Hoyos, Miami, FL (US); Rahim A. Charania, Euless, TX (US)

(73) Assignee: Cellco Partnership, Basking Ridge, NJ (US)

( * ) Notice: Subject to any disclaimer, the term of this patent is extended or adjusted under 35 U.S.C. 154(b) by 201 days.

(21) Appl. No.: 14/228,836

(22) Filed: Mar. 28, 2014

(65) Prior Publication Data

US 2015/0272825 A1     Oct. 1, 2015

(51) Int. Cl.
| | |
|---|---|
| A61J 1/03 | (2006.01) |
| B65D 55/14 | (2006.01) |
| G07C 9/00 | (2006.01) |
| A61J 1/14 | (2006.01) |
| A61J 7/00 | (2006.01) |
| A61J 7/04 | (2006.01) |
| G06F 19/00 | (2011.01) |

(52) U.S. Cl.
CPC .......... *A61J 1/03* (2013.01); *A61J 1/1412* (2013.01); *A61J 1/1437* (2013.01); *A61J 7/0076* (2013.01); *A61J 7/0481* (2013.01); *B65D 55/14* (2013.01); *G06F 19/3462* (2013.01); *G07C 9/00158* (2013.01); *G07C 9/00166* (2013.01); *A61J 2200/30* (2013.01); *A61J 2200/70* (2013.01); *A61J 2200/74* (2013.01); *A61J 2205/60* (2013.01)

(58) Field of Classification Search
CPC .......... A61J 1/03; A61J 1/1437; A61J 7/0076; A61J 7/0481; A61J 1/1412; B65D 55/14; G07C 9/00158; G07C 9/00166
See application file for complete search history.

(56) References Cited

U.S. PATENT DOCUMENTS

| | | | | |
|---|---|---|---|---|
| 2007/0156282 | A1* | 7/2007 | Dunn ................ | G06F 19/3462 700/244 |
| 2009/0294521 | A1* | 12/2009 | de la Huerga .......... | A61J 1/035 235/375 |
| 2010/0185456 | A1* | 7/2010 | Kansal ................ | G06F 19/345 705/2 |

(Continued)

OTHER PUBLICATIONS

SMRxT, Inc., "SMRxT Realtime Medication Adherence", SMRxT, Inc., Aug. 9, 2013, 3 pages.

(Continued)

*Primary Examiner* — Nabil Syed

(57) ABSTRACT

A container includes a chamber to hold a medication, a lockable lid that covers an opening of the chamber, a biometric sensor, a scale, and one or more processors. The container may store prescription information indicating how often the medication should be provided. The container may measure a weight of the medication held by the chamber using the scale. The container may receive biometric information sensed by the biometric sensor. The biometric information may indicate a biometric feature of a person attempting to open the container. The container may selectively unlock the lockable lid based on at least one of the prescription information, the weight of the medication, or the biometric information.

20 Claims, 10 Drawing Sheets

(56) References Cited

U.S. PATENT DOCUMENTS

| | | | | |
|---|---|---|---|---|
| 2014/0074283 A1* | 3/2014 | Blackburn | ............ | A61J 7/0076 |
| | | | | 700/237 |
| 2014/0262918 A1* | 9/2014 | Chu | ......................... | A61J 1/03 |
| | | | | 206/534 |
| 2015/0002606 A1* | 1/2015 | Hyde | .................. | G06F 19/3418 |
| | | | | 348/14.02 |

OTHER PUBLICATIONS

SMRxT, Inc., "SMRxT Realtime Medication Adherence", http://www.smrxt.com/index.php., 2012, 2 pages.

\* cited by examiner

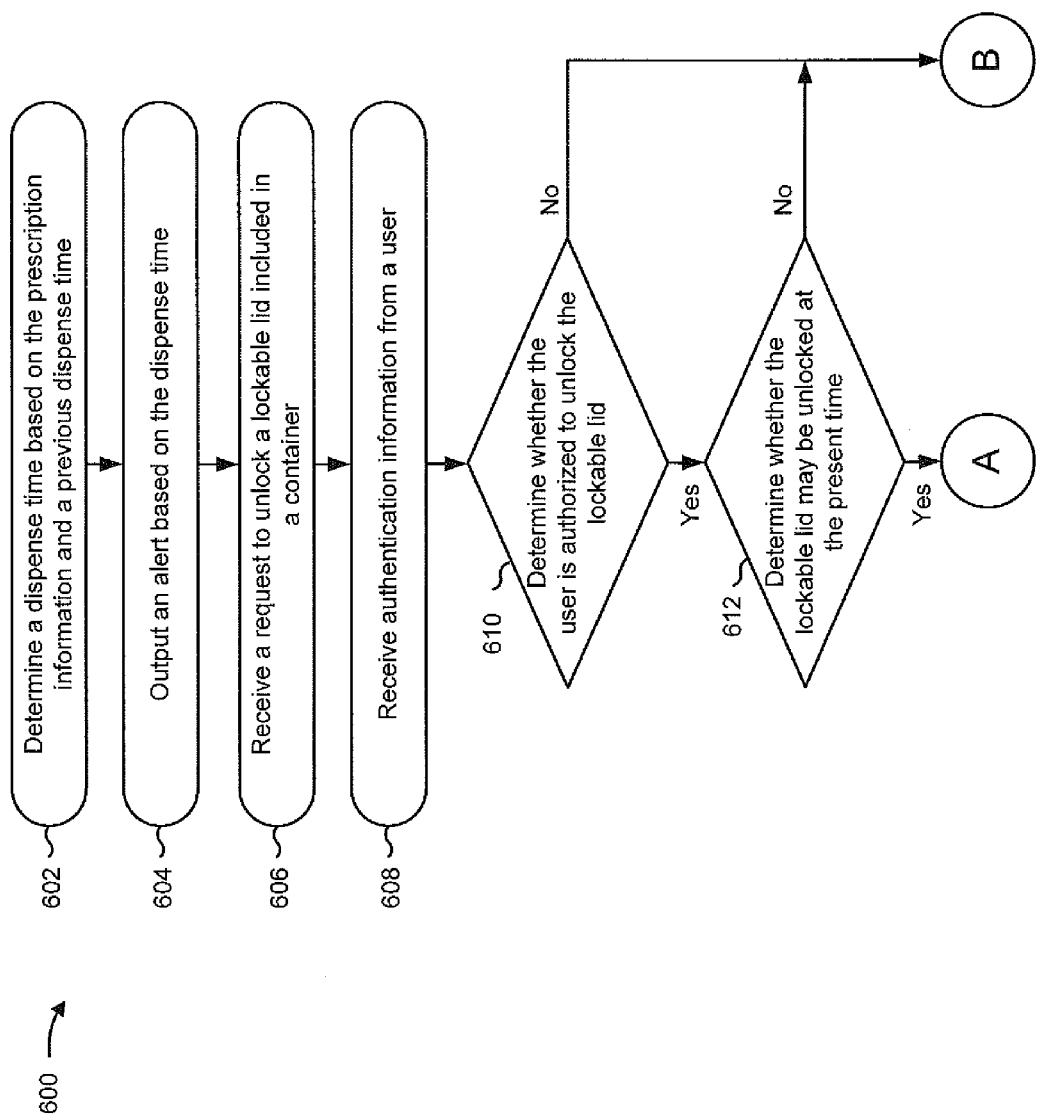

US 9,572,748 B2

PRESCRIPTION CONTAINER AND SERVICE FOR MONITORING PATIENTS

BACKGROUND

A prescription bottle contains prescribed medicine and may include a label that provides information about the medicine. Additionally, the prescription bottle may include a child resistant lid to reduce the risk of children or others inadvertently accessing the medicine inside the prescription bottle.

BRIEF DESCRIPTION OF THE DRAWINGS

FIGS. 6A and 6B are flow charts of an example process for providing access to medication held by a container;

DETAILED DESCRIPTION OF PREFERRED EMBODIMENTS

The following detailed description of example implementations refers to the accompanying drawings. The same reference numbers in different drawings may identify the same or similar elements.

A patient who keeps medication in a prescription bottle may forget to take medication at the correct time and/or intentionally or unintentionally abuse the medication by taking too much. Moreover, people who were not prescribed the medication may remove the medication from the prescription bottle even if the prescription bottle has a child resistant lid. Furthermore, people associated with the patient (e.g., a doctor, a family member, etc.) may have no way of knowing whether the patient is taking the medication as prescribed.

Implementations described herein provide a container for holding medication that may require biometric authentication, or other authentication such as voice recognition and/or an input code, to access the medication held within, thereby preventing unauthorized people from accessing the medication. Additionally, or alternatively, the container may provide reminders to a patient when it is time to take the medication and/or only permit a lid to be opened when it is time to take the medication, thereby preventing overuse and/or underuse of the medication. Furthermore, the container may determine when a patient removed medication from the container and how much medication the patient removed from the container using an included scale. In some implementations, the container may provide information about the patient's use of the medication to a service that monitors the patient's use of the medication.

Figure 1:
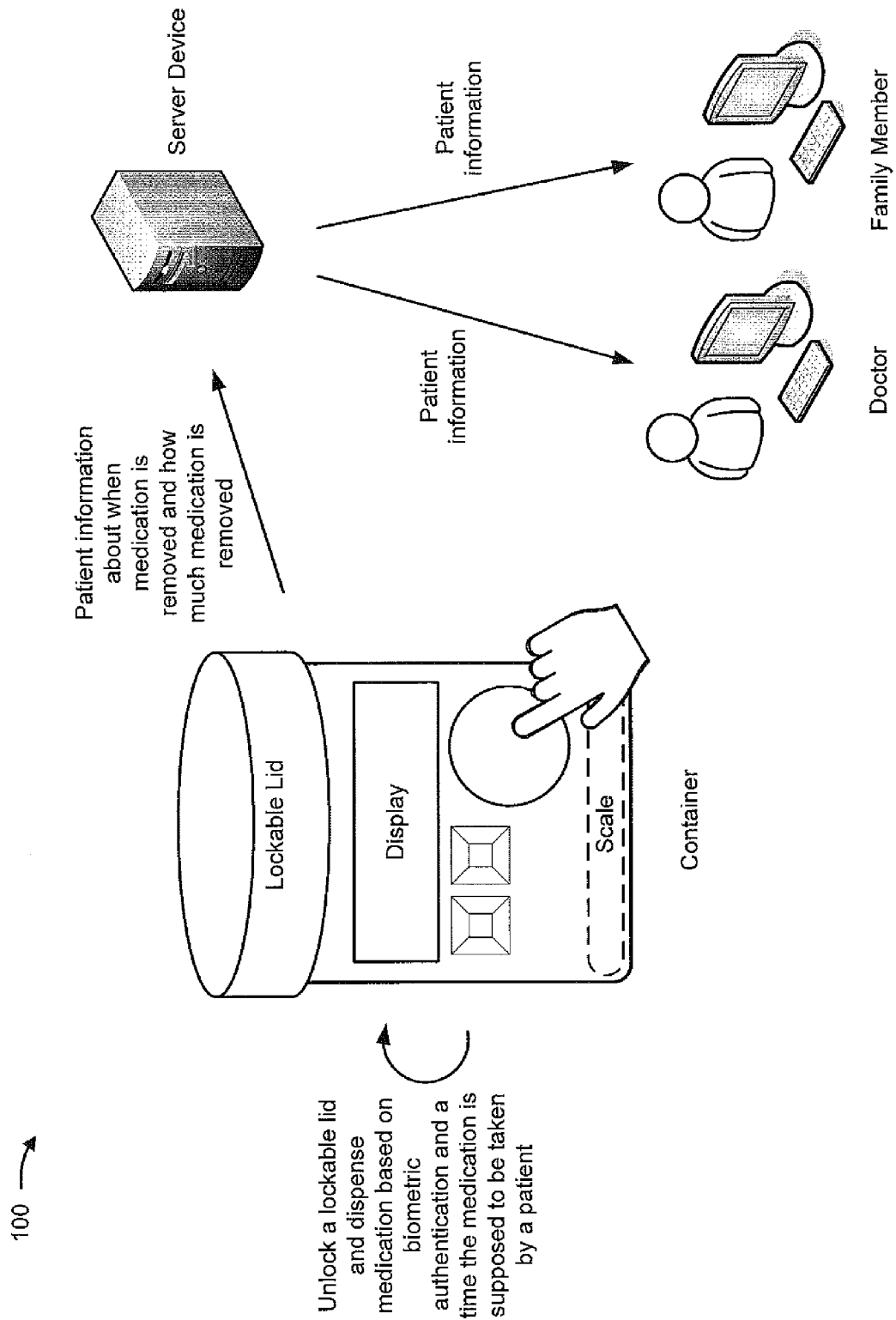
FIG. 1 is a diagram of an overview of an example implementation described herein.

FIG. 1 is a diagram of an overview of an example implementation 100 described herein. A container may include a display for displaying information about a prescription and/or for providing reminders to a patient to take a medication associated with the prescription. The container may include a lockable lid that may be electronically controlled by the container. The container may include a biometric sensor (e.g., a fingerprint scanner) for detecting a fingerprint used to authenticate a patient and unlock the lockable lid. The container may include buttons for the patient to input information into the container (e.g., a medication taken button, a volume button, a power button, etc.). Additionally, or alternatively, the container may include a scale used to weigh the medication held by the container.

In example implementation 100, assume a patient desires to unlock the lockable lid and touches the biometric sensor with a finger. The biometric sensor may detect a fingerprint of the finger and the container may determine whether the patient is authorized to unlock the lockable lid based on the fingerprint. Additionally, or alternatively, the container may store prescription information indicating when the medication may be dispensed. The container may determine whether the present time is a time the medication may be dispensed and the lockable lid may be unlocked based on the prescription information.

Assume the container determines that the lockable lid may be unlocked and the container unlocks the lockable lid. The patient may remove medication from the container. In some implementations, the container may determine how much medication was removed based on a weight measured by the scale. The container may send patient information to a server device indicating when the medication was removed and how much medication was removed. The server device may receive the patient information and send the patient information to people associated with the patient (e.g., a doctor, a family member, etc.) who are interested in monitoring the patient's use of the medication.

In this way, unauthorized people may be prevented from accessing the medication held by the container. Moreover, the container may help the patient take the medication as prescribed without overusing and/or underusing the medication. Furthermore, interested parties may be informed of whether the patient is taking the medication as prescribed.

Figure 2:
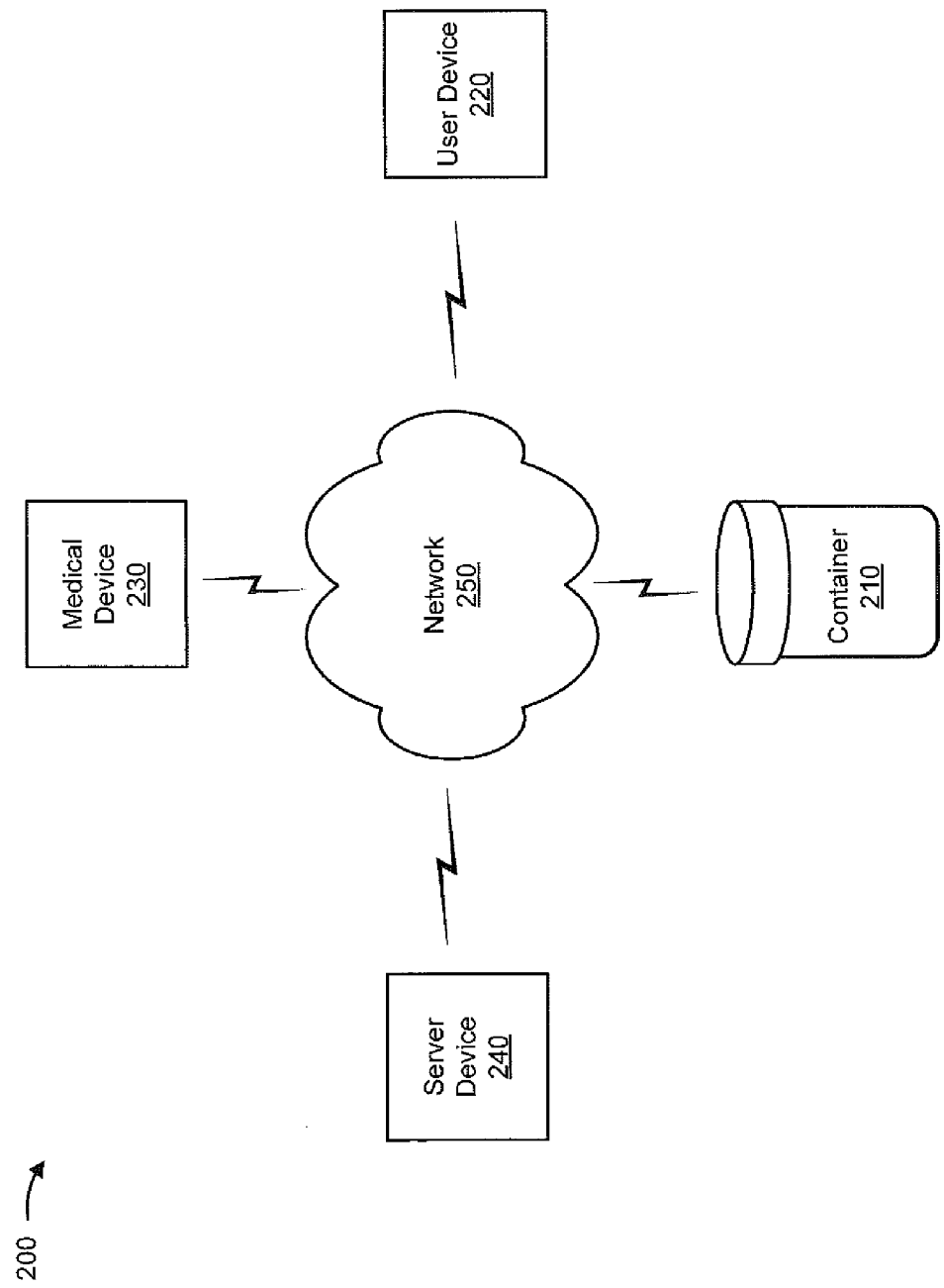
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a container 210, a user device 220, a medical device 230, a server device 240, and/or a network 250. Devices of environment 200 may interconnect via wired connections, wireless connections, or a combination of wired and wireless connections.

Container 210 may include a device capable of holding medication and capable of receiving, processing, and/or providing information. For example, container 210 may be a bottle, a vessel, a box, and/or another kind of container. In some implementations, container 210 may include a communication interface that allows container 210 to receive information from and/or transmit information to server device 240 and/or another device in environment 200, an input interface that allows a user to input information into container 210, and/or an output interface that allows container 210 to output information to a user.

User device 220 may include a device capable of receiving, processing, and/or providing information. For example, user device 220 may include a mobile phone (e.g., a smart phone, a radiotelephone, etc.), a computing device (e.g., a laptop computer, a tablet computer, a handheld computer, etc.), or a similar device. In some implementations, user device 220 may include a communication interface that allows user device 220 to receive information from and/or transmit information to server device 240 and/or another device in environment 200.

Medical device 230 may include a device capable of sensing biometric and/or health-related information of a patient. For example, medical device 230 may be a scale, a heart rate monitor, a blood pressure meter, a blood glucose meter, a breathalyzer, a biometric patch, a thermometer, etc. In some implementations, medical device 230 may include a communication interface that allows medical device 230 to receive information from and/or transmit information to server device 240 and/or another device in environment 200.

Server device 240 may include one or more devices capable of processing and/or routing information. In some implementations, server device 240 may include a communication interface that allows server device 240 to receive information from and/or transmit information to other devices in environment 200. Server device 240 may manage a service for monitoring patients and medications.

Network 250 may include one or more wired and/or wireless networks. For example, network 250 may include a cellular network, a public land mobile network (PLMN), a local area network (LAN), a wide area network (WAN), a metropolitan area network (MAN), a telephone network (e.g., the Public Switched Telephone Network (PSTN)), an ad hoc network, an intranet, the Internet, a fiber optic-based network, a satellite network, a cloud computing network, and/or a combination of these or other types of networks.

The number and arrangement of devices and networks shown in FIG. 2 is provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
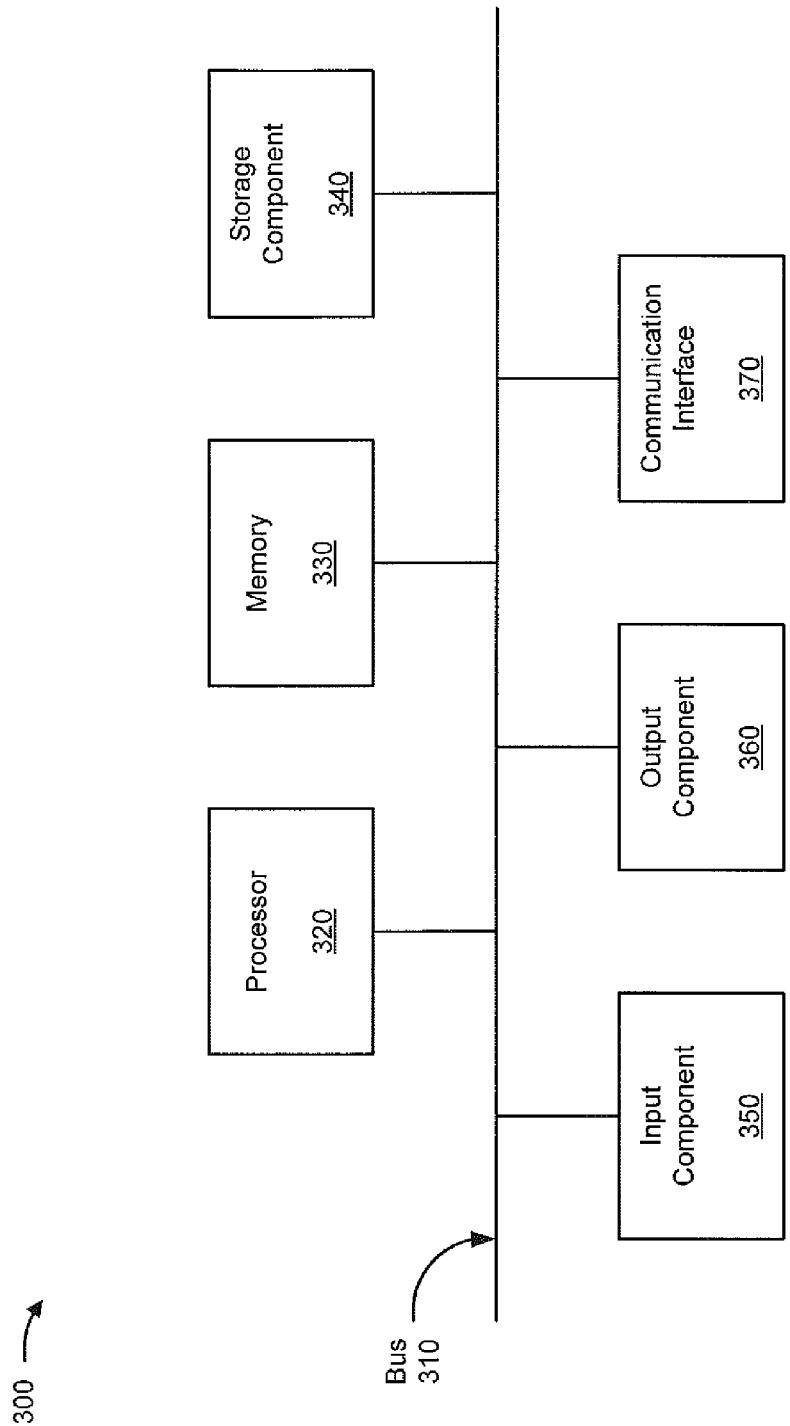
FIG. 3 is a diagram of example components of one or more devices of FIG. 2.

FIG. 3 is a diagram of example components of a device 300. Device 300 may correspond to container 210, user device 202, medical device 230, and/or server device 240. In some implementations, container 210, user device 202, medical device 230, and/or server device 240 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 may include a component that permits communication among the components of device 300. Processor 320 may include a processor (e.g., a central processing unit (CPU), a graphics processing unit (GPU), an accelerated processing unit (APU), etc.), a microprocessor, and/or any processing component (e.g., a field-programmable gate array (FPGA), an application-specific integrated circuit (ASIC), etc.) that interprets and/or executes instructions. Memory 330 may include a random access memory (RAM), a read only memory (ROM), and/or another type of dynamic or static storage device (e.g., a flash memory, a magnetic memory, an optical memory, etc.) that stores information and/or instructions for use by processor 320.

Storage component 340 may store information and/or software related to the operation and use of device 300. For example, storage component 340 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 350 may include a component that permits device 300 to receive information, such as via user input (e.g., a touch screen display, a keyboard, a keypad, a mouse, a button, a switch, a microphone, a biometric sensor, etc.). Additionally, or alternatively, input component 350 may include a sensor for sensing information (e.g., a global positioning system (GPS) component, an accelerometer, a gyroscope, an actuator, etc.). Output component 360 may include a component that provides output information from device 300 (e.g., a display, a speaker, one or more light-emitting diodes (LEDs), etc.).

Communication interface 370 may include a transceiver-like component (e.g., a transceiver, a separate receiver and transmitter, etc.) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may be used to send and/or receive information indicating text, pictures, charts, graphs, voice data, voice recordings, and/or synthesized voice data. In some implementations, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 is provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
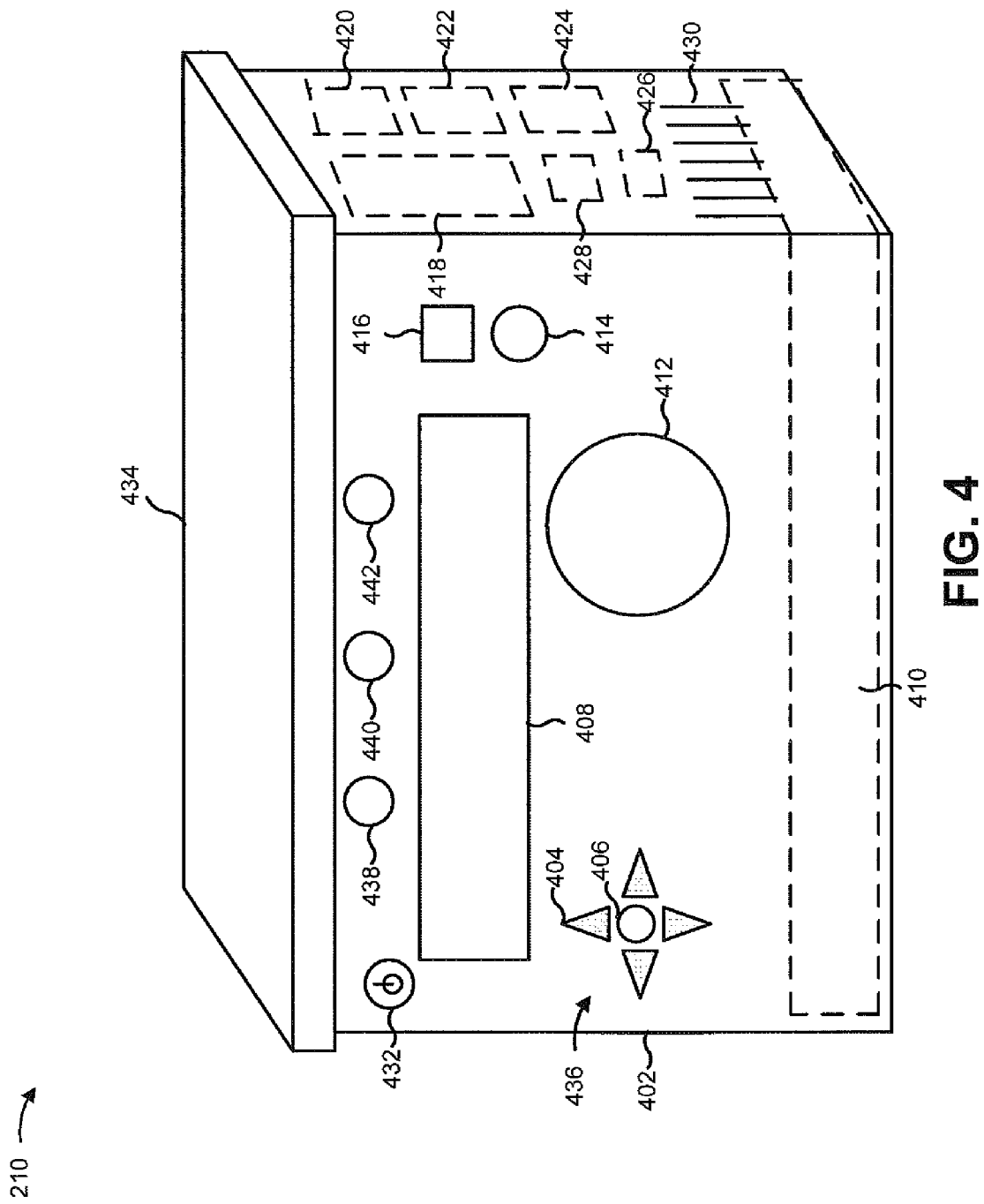
FIG. 4 is diagram of example components of a container of FIG. 2.

FIG. 4 is diagram of example components of container 210 of FIG. 2. As shown in FIG. 4, container 210 may include a housing 402, a directional button 404, a select button 406, a display 408, a scale 410, a biometric sensor 412, a microphone 414, an indicator light 416, a battery 418, a processor 420, a memory 422, a storage device 424, a communication device 426, a GPS device 428, a speaker 430, a power button 432, a lockable lid 434, a chamber 436, a medication taken button 438, a calibration button 440, and/or an emergency button 442.

Housing 402 may include a casing that provides structural support for container 210. Housing 402 may be comprised of a plastic material, a metal material, a glass material, and/or another material.

Directional button 404 may be a button that allows a user to move a cursor displayed on display 408, scroll through options displayed on display 408, and/or provide other kinds of input. Container 210 may include more than one directional button 404 for different directions (e.g., four directional buttons as shown in FIG. 4). Select button 406 may be a button that allows a user to input a selection and/or select an option displayed on display 408. A user may use directional button(s) 404 in combination with select button 406 to enter inputs. Display 408 may include a LED display, a LCD display, a plasma display, and/or any other kind of display. Display 408 may include a touch screen that allows a user to provide inputs. In some implementations, directional button(s) 404, select button 406, and/or display 408 may be used to input authentication information (e.g., a password, a personal identifier number (PIN), etc.) for authenticating a user.

Scale 410 may measure a weight of medication placed inside container 210. Scale 410 may be located on an inside, bottom surface of housing 402. In some implementations, scale 410 may cover the entire inside, bottom surface of housing 402. A top surface of scale 410 may be a bottom surface of chamber 436. In some implementations, container 210 may include more than one scale located on more than one surface and/or more than one portion of the bottom surface of chamber 436. For example, each inside surface of chamber 436 and/or an inside surface of lockable lid 434 may include a scale. Thus, a user may set container 210 down on any surface of container 210 and a weight of medication held therein may be measured. Additionally, or alternatively, container 210 may include a gyroscope (not shown) used to determine which scale 410 is parallel to the ground and should be used to measure the weight of the medication.

Biometric sensor 412 may be a biometric device that identifies a biometric feature of a user (e.g., a fingerprint, an eye pattern, a vein pattern, etc.). For example, biometric sensor 412 may be a fingerprint scanner that detects a fingerprint and/or a vein pattern of a user. Additionally, or alternatively, biometric sensor 412 may be a camera used for facial recognition or ocular recognition of an eye pattern. In some implementations, a biometric feature may be used as authentication information to authenticate the user. Microphone 414 may be a device that detects and/or records sound. The microphone may be used for voice recognition and/or to detect an audio password. In some implementations, voice recognition and/or an audio password may be used to authenticate the user.

Indicator light 416 may be any kind of light (e.g., a LED) used to provide indications to a user. For example, indicator light 416 may be used to indicate an alert to a user (e.g., access to medications granted, access to medications denied, new message received, time to take medication, etc.).

Battery 418 may provide power for operating container 210. Battery 418 may be rechargeable or non-rechargeable. In some implementations, battery 418 may be recharged via inductive charging.

Processor 420 may correspond to processor 320 of FIG. 3. Memory 422 may correspond to memory 330 of FIG. 3. Storage device 424 may correspond to storage component 340 of FIG. 3. Communication device 426 may correspond to communication component 360 of FIG. 3. GPS device 428 may be used to determine a location of container 210. As shown in FIG. 4, processor 420, memory 422, storage device 424, communication device 426, and/or GPS device 428 may be located within a surface of housing 402.

Speaker 430 may be used to output sound. For example, speaker 430 may be used to indicate an alert to a user (e.g., access to medications granted, access to medications denied, new message received, time to take medication, etc.). Power button 432 may be used to turn on and turn off container 210.

Lockable lid 434 may be a lid that covers an opening of chamber 436. Lockable lid 432 may be electronically controlled by processor 420 to lock and unlock. When unlocked, lockable lid 434 may be removed from housing 402 to provide a user access to chamber 436 and medication contained therein. In some implementations, lockable lid 434 may be detachable from housing 402 and may be detached to provide access to chamber 436. Additionally, or alternatively, lockable lid 434 may be attached to housing 402 by a hinge (not shown) or another type of connector. Lockable lid 434 may rotate about the hinge when unlocked to provide a user access to chamber 436. Additionally, or alternatively, lockable lid 434 may include a door (not shown) that covers a slot. The door may rotate about a hinge (not shown) and/or slide to uncover the slot when unlocked and provide access to chamber 436.

Chamber 436 may be a concave shaped interior portion of housing 402 that may hold medication. Lockable lid 434 may cover an opening of chamber 436. Lockable lid 434 may be moved to uncover the opening and provide a user access to medication held by chamber 436.

Medication taken button 438 may be a button that silences reminders and/or confirms the patient took the medication. Medication taken button 438 may also be used to indicate medications that cannot be transferred into container 210 were taken by the patient.

Calibration button 440 may be a button used in conjunction with scale 410 to determine the weight of medication. For example, calibration button 400 may use used to determine the weight of a single dose of medication.

Emergency button 442 may be button that causes container 210 to transmit an emergency signal and provide location information to emergency services. For example, emergency button 442 may transmit an emergency message to a hospital, a police station, a fire department, a family member, a healthcare professional, etc.

In some implementations, container 210 may include a designated space (not shown) to attach a sticker including prescription information. Additionally, or alternatively, container 210 may include a clip used to attach container 210 to an article of clothing. Container 210 may be waterproof and may come in multiple colors. Moreover, container 210 may be reusable.

The shape of container 210 is not limited to that shown in FIG. 4 and may be any shape capable of enclosing chamber 436 and holding medication. In some implementations, container 210 may be shaped to have only one flat surface that includes scale 410. Accordingly, a user may only be able to set container 210 down flat on the one surface. Thus, a shape with only one flat surface may ensure that the medication is always resting on top of scale 410 and the medication is not resting on another surface when scale 410 measures the weight of the medication. For example, housing 402 and lockable lid 434 may combine to make a cone shape. Lockable lid 434 may be at the top of the cone shape and a flat bottom surface of housing 402 may be at the bottom of the cone shape. Additionally, or alternatively, housing 402 and lockable lid 434 may combine to make a dome shape. Lockable lid 424 may be at the top of the dome and a flat bottom surface of housing 402 may be at the bottom of the dome shape.

The number and arrangement of components shown in FIG. 4 is provided as an example. In practice, container 210 may include differently arranged components than those shown in FIG. 4. For example, directional button 404, select button 406, display 408, scale 410, biometric sensor 412, microphone 414, indicator light 416, battery 418, processor 420, memory 422, storage device 424, communication device 426, GPS device 428, speaker 430, power button 432, medication taken button 438, calibration button 440, and/or emergency button 442 may be arranged on any surface of housing 402 and/or lockable lid 434. In some implementations, container 210 may include additional components, fewer components, and/or different components than those shown in FIG. 4. For example, container 210 may include a keyboard, a number pad, volume buttons, etc. Additionally, or alternatively, a set of components (e.g., one or more components) of container 210 may perform one or more functions described as being performed by another set of components of container 210.

Figure 5:
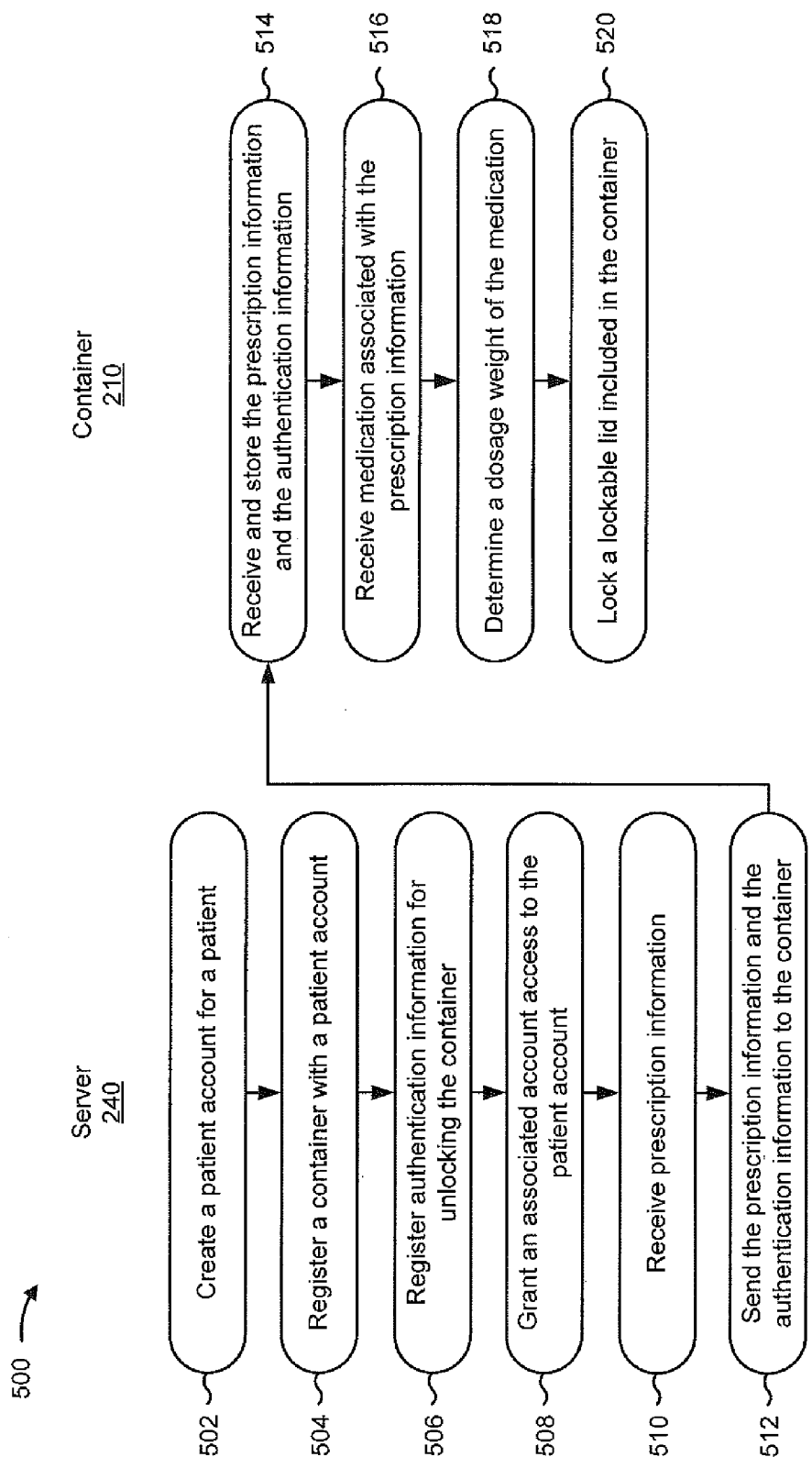
FIG. 5 is a flow chart of an example process for preparing a container to receive medication.

FIG. 5 is a flow chart of an example process 500 for preparing container 210 to receive medication. In some implementations, one or more process blocks of FIG. 5 may be performed by container 210 and/or server device 240. In some implementations, one or more process blocks of FIG. 5 may be performed by another device or a group of devices separate from or including container 210 and/or server device 240, such as user device 220 and/or medical device 230.

As shown in FIG. 5, process 500 may include creating a patient account for a patient (block 502). For example, server device 240 may create the patient account for the patient.

In some implementations, server device 240 may provide and operate an application for generating, managing, and accessing accounts. For example, the application may correspond to a website, a web application, and/or a mobile application that users may access. As used herein, the term "user" may refer to a patient, a family member, a caregiver, a healthcare provider, and/or any other user affiliated with the patient account. A user may use user device 220 to access the application and send a request to create a patient account to server device 240. The user, via user device 220, may send account information specifying login information for logging into the account (e.g., a username, a password, biometric information, etc.), a name, and/or contact information (e.g., an email address, a phone number, etc.).

Server device 240 may receive the request and the account information. Server device 240 may create the patient account based on the request by creating an entry for the patient account in an account data structure stored in a memory of server device 240 and/or a memory accessible by server device 240. The patient account (e.g., the entry) may associate the login information, the name, and the contact information.

Server device 240 may create multiple patient accounts for multiple patients and may generate a respective entry in the account data structure for each patient account.

Additionally, or alternatively, server device 240 may create other accounts for users other than patients. For example, server device 240 may create accounts for family members, caregivers, and/or healthcare providers.

As further shown in FIG. 5, process 500 may include registering container 210 with the patient account (block 504). For example, server device 240 may register container 210 with the patient account.

A user may log into the patient account by accessing the application via user device 220 and inputting the login information (e.g., a username, a password, etc.). User device 220 may receive the login information input by the user and send the login information to server device 240. Server device 240 may receive the login information and authenticate the user based on the login information. For example, server device 240 may compare the received login information with login information associated with the patient account. If the received login information matches the login information associated with the patient account, server device 240 may allow the user to access the patient account.

The user may input a container identifier (ID) into user device 220 that identifies a container 210 to be registered with the patient account. User device 220 may send a request to server device 240 to register container 210. The request may include the container ID that uniquely identifies container 210 to be added. Server device 240 may receive the request and register container 210 by storing the container ID in the entry in the account data structure for the patient account. One or more containers 210 may be registered with the patient account.

In some implementations, the user may have to verify the user is in possession of container 210 to register container 210 with the patient account. Server device 240 may send a verification code to container 210 based on the container ID and container 210 may receive the verification code. The verification code may be a string of characters of any length. Container 210 may display the verification code on an included display. The user may read the verification code and input the verification code into user device 220. User device 220 may send the verification code to server device 240 and server device 240 may receive the verification code. If the verification code received from user device 220 matches the verification code sent to container 210, server device 240 may register container 210 with the patient account.

As further shown in FIG. 5, process 500 may include registering authentication information for unlocking container 210 (block 506). For example, server device 240 may register the authentication information.

The authentication information may include a password (e.g., a string of characters of any length), an audio password (e.g., a recorded sound and/or voice), and/or biometric feature information (e.g., data representing a fingerprint, an eye pattern, a face pattern, a vein patter, etc.) used to unlock a lockable lid of container 210 (e.g., lockable lid 434). The user may input the authentication information into user device 220 and/or container 210. For example, the user may operate buttons (e.g., a keyboard) included in user device 220 and/or container 210 to type a password; operate a microphone included in user device 220 and/or container 210 to record an audio password; and/or operate a biometric sensor included in user device 220 and/or container 210 to input the biometric feature information. User device 220 and/or container 210 may send the authentication information to server device 240 and server device 240 may receive the authentication information. Server device 240 may register the authentication information with the patient account by storing the authentication information in the entry in the account data structure for the patient account.

As further shown in FIG. 5, process 500 may include granting an associated user access to the patient account (block 508). For example, server device 240 may grant a different user (e.g., another patient, a family member of the patient, a caregiver, and/or a healthcare professional) access to the patient account.

The patient may use user device 220 to send information to server device 240 that identifies a user that may be granted access to the patient account and identifies an access level for the user. Server device 240 may receive the information and grant the user access to the account at a certain access level. For example, the access levels may include a caregiver access level, a family member access level, and/or a healthcare professional access level.

A caregiver access level may be granted to a caregiver of the patient (e.g., the user associated with the patient account). In some implementations, the caregiver access level may grant full access to the patient's medical information (e.g., medical records, prescription information, status information sent from container 210, etc.). However, the caregiver access level may not grant access to the patient's personal information (e.g., phone number, address, payment information, etc.).

A family member access level may be granted to a family member of the patient. In some implementations, the family member access level may grant access to prescription information, status information sent from container 210, and/or comments input by a healthcare professional and/or the patient. Additionally, or alternatively, the family member access level may grant access to alerts regarding usage of medication (e.g., an under and/or over use of the medication).

A healthcare processional access level may be granted to a healthcare professional. In some implementations, the healthcare professional access level may grant full access to the patient's medical information and allow the healthcare processional to upload comments to the patient account that may be accessed by the patient and/or another authorized user. Additionally, or alternatively, a family member access level and/or a caregiver access level may allow a user to upload comments to the patient account.

Additionally, or alternatively, other permissions may be given to users. For example, a user may be granted permission to locate container 210 using GPS. As another example, a user may be allowed to unlock container 210 remotely via server device 240 and/or locally at container 210 (e.g., a family member may use the family member's own finger to unlock container 210). Authentication information associated with the user (e.g., a biometric feature information associated with a user other than the patient) may be registered with the patient account, and the user other than the patient may unlock container 210. In this way, other users besides the patient may be allowed to unlock container 210 while still minimizing any unauthorized access or tampering with container 210.

As further shown in FIG. 5, process 500 may include receiving prescription information (block 510). For example, server device 240 may receive the prescription information.

A user may input the prescription information into user device 220. The prescription information may identify a medication name, a dosage of the medication (e.g., a quantity of pills, a quantity of liquid, etc.), a frequency at which the medication is to be taken (e.g., every 12 hours, every 24 hours, etc.), a concentration of the medication, refill information (e.g., how many refills are permitted), pharmacy information (e.g., a pharmacy name, a phone number, an email address, etc.), special instructions (e.g., take medication with food), a side effect associated with the medication, a drug interaction associated with the medication, or the like. User device 220 may send the prescription information to server device 240. Additionally, or alternatively, a pharmacist or other medical professional may send the prescription information to server device 240. Server device 240 may receive the prescription information and may register the prescription information by storing the prescription information in the entry in the account data structure for the patient account.

As further shown in FIG. 5, process 500 may include sending the prescription information and the authentication information to container 210 (block 512). For example, server device 240 may send the prescription information and the authentication information to container 210 registered with the patient account.

As further shown in FIG. 5, process 500 may include receiving and storing the prescription information and the authentication information (block 514). For example, container 210 may receive the prescription information and the authentication information sent from server device 240, and store the prescription information and the authentication information in a memory included in container 210.

Additionally, or alternatively, a user (e.g., the patient) may input the prescription information and the authentication information into container 210, rather than container 210 receiving the prescription information and the authentication information from server device 240. For example, the user may input the prescription information and the authentication information using input components included in container 210 (e.g., a button, a touch screen, a keyboard, a microphone, a biometric sensor, etc.). In some implementations, container 210 may operate independently of server device 240 and may not communicate with server device 240.

As further shown in FIG. 5, process 500 may include receiving medication associated with the prescription information (block 516). For example, a user may insert medication (e.g., pills, liquid, cream, etc.) into a chamber included in container 210 and container 210 may receive the medication.

As further shown in FIG. 5, process 500 may include determining a dosage weight of medication (block 518). For example, container 210 may determine the dosage weight of the medication. The dosage weight of the medication may be the weight of a single dose of the medication (e.g., a weight of one pill, a weight a single serving of liquid, etc.).

The user may push a button (e.g., a calibrate button) and container 210 may measure the weight of the medication using a scale included in container 210. The user may input a quantity of doses of the medication inserted into container 210 using input components of container 210. For example, the user may input a number of pills inserted into container 210 and/or a number of doses of liquid inserted into container 210. Container 210 may determine the dosage weight of the medication based on the quantity of doses of the medication and the weight of the medication. For example, container 210 may divide the weight of the medication by the quantity of doses to determine the dosage weight of the medication.

Container 210 may store information indicating the dosage weight of the medication in a memory included in container 210. The user may insert any remaining medication into container 210 after the dosage weight has been determined.

As further shown in FIG. 5, process 500 may include locking a lockable lid included in container 210 (block 520). For example, the user may close the lockable lid and container 210 may lock the lockable lid preventing access to the medication held by container 210.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6B:
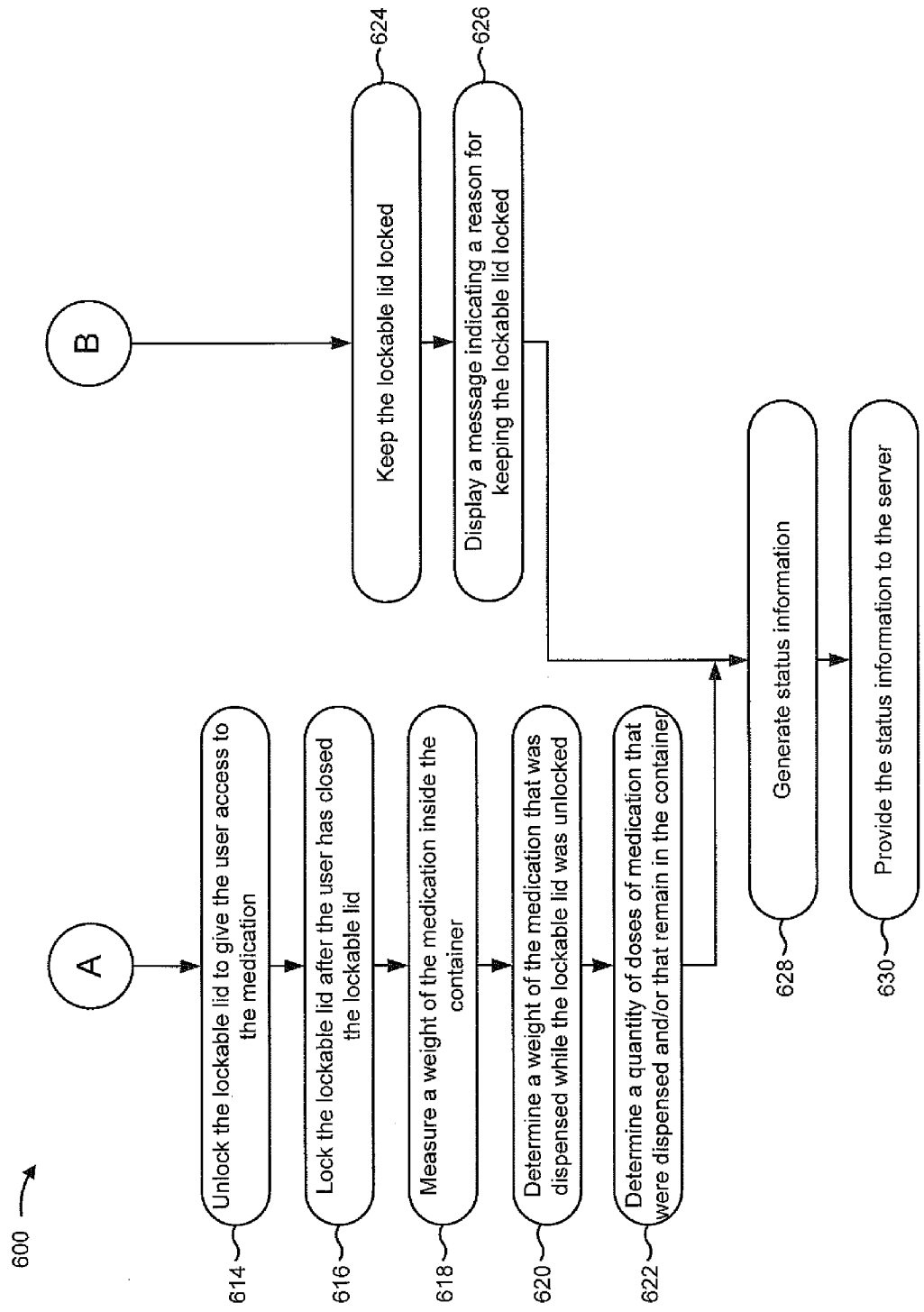

FIGS. 6A and 6B are flow charts of an example process 600 for providing access to medication held by container 210. In some implementations, one or more process blocks of FIGS. 6A and 6B may be performed by container 210. In some implementations, one or more process blocks of FIGS. 6A and 6B may be performed by another device or a group of devices separate from or including container 210, such as user device 220, medical device 230, and/or server device 240.

As shown in FIG. 6A, process 600 may include determining a dispense time based on the prescription information and a previous dispense time (block 602). For example, container 210 may determine the dispense time. The dispense time may represent a next or subsequent time to dispense medication from container 210. In some implementations, the dispense time may be a range of time. Container 210 may determine the length of the range of time based on the prescription information. Additionally, or alternatively, container 210 may determine the length of the range of time based on information input by the user to configure the range of time. For example, the patient may define the range of time using the application and/or website provided by server device 240.

The prescription information may indicate a frequency at which the medication is to be taken by a patient (e.g., every 12 hours, every 24 hours, etc.). The previous dispense time may indicate the most recent time that medication was dispensed from container 210 and/or should have been dispensed from container 210 (e.g., if a user misses a dose of medication). Container 210 may determine the dispense time by adding a length of time indicated by the frequency (e.g., 12 hours, 24 hours, etc.) to the previous dispense time. For example, assume the medication is to be taken every 8 hours and the previous dispense time was 1:00 PM. Accordingly, the time to dispense medication would be 8 hours later at 9:00 PM. Moreover, the patient may input preferred times to dispense the medication using the application and/or website provided by server device 240. Server device 240 may provide information indicating the preferred times to container 210 and container 210 may determine the dispense time based on the preferred times. Accordingly, the patient may be given some flexibility as to when the medication is dispensed.

Additionally, or alternatively, the prescription information may indicate what happens if the patient misses a dose of medication (e.g., container 210 does not dispense the medication at the dispense time and/or during a range around the dispense time). For example, the prescription information may indicate that the patient should take two doses of the medication at the dispense time if the previous dose was missed. Additionally, or alternatively, the prescription information may indicate that the patient should skip the missed dose and should take a single dose of the medication at the dispense time. Thus, container 210 may determine a quantity of medication or a number of doses of medication that should be dispensed at the dispense time.

As further shown in FIG. 6A, process 600 may include outputting an alert based on the dispense time (block 604). For example, container 210 may output the alert at the dispense time and/or a particular amount of time before the dispense time (e.g., as a reminder to the patient that it is almost time to take the medication). The alert may indicate a time for the patient to take a dose of the medication. Additionally, or alternatively, the alert may indicate a quantity of medication to take and/or a quantity of doses of medication to take.

In some implementations, container 210 may output alerts at particular time intervals after the dispense time if the medication was not dispensed at the dispense time. In other words, if the patient fails to remove the medication from container 210 at the dispense time, container 210 may output alerts or reminders that the medication needs to be taken. In some implementations, if the patient does not acknowledge the alert (e.g., press a button on container 210) within a particular period of time, container 210 may send an alert to another user associated with the account (e.g., a family member) indicating that a dose was missed.

Container 210 may output the alert by displaying a message on a screen (e.g., "time to take your medication," "take two pills in 15 minutes," etc.), turning on an indicator light, flashing an indicator light, changing the color of an indicator light, and/or emitting a sound from speakers included in container 210. In some implementations, container 210 and/or server device 240 may provide alerts to other devices based on contact information associated with the patient account. For example, container 210 and/or server device 240 may cause a text message to be sent to a patient's mobile phone and/or an email to be sent to an email address associated with the patient.

As further shown in FIG. 6A, process 600 may include receiving a request to unlock the lockable lid included in container 210 (block 606). For example, container 210 may receive the request to unlock the lockable lid based on a user input.

In some implementations, the user may input the request by pressing an unlock button included in container 210. Additionally, or alternatively, the user may input the request to unlock the lockable lid by providing biometric feature information to a biometric sensor included in container 210, by entering a password via buttons and/or a touchscreen included in container 210, and/or inputting an audible password using a microphone included in container 210.

As further shown in FIG. 6A, process 600 may include receiving authentication information from a user (block 608). For example, container 210 may receive the authentication information, such as a password (e.g., a string of characters of any length), an audio password (e.g., a recorded sound and/or voice), and/or biometric feature information (e.g., data representing a biometric feature) used to unlock a lockable lid of container 210.

The user may input the authentication information by providing the biometric feature information to the biometric sensor included in container 210 (e.g., touching a finger to a fingerprint scanner), by entering a password via buttons and/or a touchscreen included in container 210, and/or inputting an audible password using a microphone included in container 210. Container 210 may receive the input authentication information.

As further shown in FIG. 6A, process 600 may include determining whether the user is authorized to unlock the lockable lid (block 610). For example, container 210 may determine whether the user is authorized to unlock the lockable lid based on the received authentication information input by the user and the stored authentication information.

Container 210 may compare the received authentication information with stored authentication information. For example, container 210 may compare biometric feature information input by the user via the biometric sensor with biometric feature information for an authorized user stored in a memory of container 210. If the received authentication information matches the stored authentication information, then container 210 may determine that the user is authorized to unlock the lockable lid. If the received authentication information does not match the stored authentication information, then container 210 may determine that the user is not authorized to unlock the lockable lid.

In some implementations, container 210 may send the received authentication information to server 240 and server 240 may determine whether the user is authorized to unlock the lockable lid. Server 240 may send a determination results to container 210 and container 210 may receive the determination result.

As further shown in FIG. 6A, when user is authorized to unlock the lockable lid (block 610—yes), process 600 may include determining whether the lockable lid may be unlocked at a present time (block 612). For example, container 210 may determine whether the lockable lid may be unlocked at a present time (e.g., a time the request to unlock the lockable lid is received).

In some implementations, container 210 may determine that the lockable lid may be unlocked when the present time is the same as or later than the dispense time.

In some implementations, container 210 may calculate a range around the dispense time during which the lockable lid may be unlocked. For example, container 210 may add a particular amount of time (e.g., 30 minutes, 1 hour, 2 hours, etc.) before the dispense time and/or after the dispense time to calculate the range. For instance, assume the dispense time is 9:00 PM. Container 210 may calculate a range from 8:00 PM to 10:00 PM that the lockable lid may be unlocked. Container 210 may determine that the lockable lid may be unlocked when the present time is within the range around the dispense time.

When the lockable lid may be unlocked (block 612—yes), process 600 may include unlocking the lockable lid to give the user access to the medication (block 614) (FIG. 6B). For example, container 210 may unlock the lockable lid. In some implementations, a processor included in container 210 may send a signal to the lockable lid instructing the lockable lid to unlock. The lockable lid may receive the signal and unlock based on the signal.

In some implementations, before unlocking the lockable lid, container 210 may measure a weight of the medication held inside container 210 using a scale included in container 210. Container 210 may store information indicating the weight of the medication at this time.

A user may open and/or remove the lockable lid to access the medication held inside container 210. The user may remove medication held inside container 210. The user may close and/or replace the lockable lid.

As further shown in FIG. 6B, process 600 may include locking the lockable lid after the user has closed the lockable lid (block 616). For example, container 210 may lock the lockable lid based on detecting that the lockable lid has closed. Additionally, or alternatively, user device 220, medical device 230, and/or server device 240 may send an instruction to container 210 to lock the lockable lid. Container 210 may receive the instruction and lock the lockable lid based on receiving the remotely sent instruction. In some implementations, a processor included in container 210 may send a signal to the lockable lid instructing the lockable lid to lock. The lockable lid may receive the signal and lock based on the signal.

As further shown in FIG. 6B, process 600 may include measuring a weight of the medication held by container 210 (block 618). For example, container 210 may measure a weight of the medication inside container 210 using a scale included in container 210. Container 210 may store information indicating the weight of the medication at this time.

In some implementations, container 210 may determine an orientation of container 210 before measuring the weight of the medication using a gyroscope included in container 210. For example, container 210 may only measure the weight of the medication when the orientation of container 210 indicates that the medication is resting on the scale and not another surface of container 210.

As further shown in FIG. 6B, process 600 may include determining a weight of medication that was dispensed while the lockable lid was unlocked based on the measured weight of the medication (block 620). For example, container 210 may determine the weight of the medication that was dispensed while the lockable lid was unlocked.

Container 210 may determine the weight of the medication that was dispensed based on a difference between a weight of the medication measured after the lockable lid was locked at block 616 and a weight of the medication measured before the lockable lid was unlocked (e.g., as measured at block 614 and/or as measured after the previous time the lockable lid was locked).

Container 210 may determine medication was dispensed if the weight of the medication measured after the lockable lid was locked in block 616 is less than the weight of the medication measured before the lockable lid was unlocked. If container 210 determines medication was dispensed, container 210 may determine a new dispense time that the medication should be dispensed. Moreover, a display included in container 210 may display encouraging messages to the patient (e.g., "good job taking your medication!").

Container 210 may determine no medication was dispensed if the weight of the medication measured after the lockable lid was locked in block 616 is the same as the weight of the medication measured before the lockable lid was unlocked. If container 210 determines medication was not dispensed, container 210 may output an alert indicating that the user did not remove any medication.

Container 210 may determine that medication was added to container 210 if the weight of the medication measured after the lockable lid was locked in block 616 is greater than the weight of the medication measured before the lockable lid was unlocked.

As further shown in FIG. 6B, container 210 may determine a quantity of doses of medication that were dispensed from container 210 and a quantity of doses of medication that remain inside of container 210 (block 622). For example, container 210 may determine a quantity of doses of medication that were dispensed from container 210 based on the weight of the medication dispensed and a dosage weight of the medication determined at block 518 of FIG. 5.

Additionally, or alternatively, container 210 may determine a quantity of doses of medication that remain inside of container 210 based on the weight of the medication measured after the lockable lid was locked in block 616 and the dosage weight of the medication determined at block 518 of FIG. 5. If the quantity of doses of medication remaining inside of container 210 satisfies a threshold level (e.g., below a certain number of doses remaining), container 210 may output an alert indicating the need for a refill to be ordered. In some implementations, container 210 may automatically request a refill by sending a request to a pharmacy identified by the prescription information. In some implementations, the prescription information may indicate that no more refills are available. Accordingly, container 210 may output an alert indicating that the user should obtain a new prescription.

As further shown in FIG. 6A, when the user is not authorized to unlock the lockable lid and/or the lockable lid may not be unlocked at the present time (block 612—no), process 600 may include keeping the lockable lid locked (block 624) (FIG. 6B). For example, container 210 may keep the lockable lid locked.

As further shown in FIG. 6B, process 600 may include displaying a message indicating a reason for keeping the lockable lid locked (block 626). For example, container 210 may display the message indicating the reason on a display included in container 210. The reasons for keeping the lockable lid locked may include a user not being authorized to unlock the lockable lid, an incorrect password being entered, the present time not being a time medication may be accessed, etc. Additionally, or alternately, container 210 may display a message indicating the next time the lockable lid may be unlocked.

As further shown in FIG. 6B, process 600 may include generating status information (block 628). For example, container 210 may generate the status information.

If the lockable lid was unlocked at block 614, the status information may indicate who unlocked the lockable lid (e.g., if a biometric feature was used as authentication information), what time and/or date the lockable lid was unlocked, whether any medication was removed from container 210 while the lockable cap was unlocked, how many doses of medication were removed from container 210, how many doses of medication remain in container 210, etc.

If the lockable lid was kept locked at block 624, the status information may indicate who attempted to unlock the lockable lid (e.g., if container 210 recognized the biometric feature), a time and/or date the user attempted to unlock the lockable lid, a reason why the lockable lid was kept locked, etc.

The status information may also include information indicating a dispense time and/or whether a user missed a dose of medication at a dispense time.

As further shown in FIG. 6B, process 600 may include sending the status information to server device 240 (block 630). For example, container 210 may send the status information to server device 240.

Although FIGS. 6A and 6B show example blocks of process 600, in some implementations, process 600 may include additional blocks, fewer blocks, different blocks, or differently arranged blocks than those depicted in FIGS. 6A and 6B. Additionally, or alternatively, two or more of the blocks of process 600 may be performed in parallel.

Figure 7:
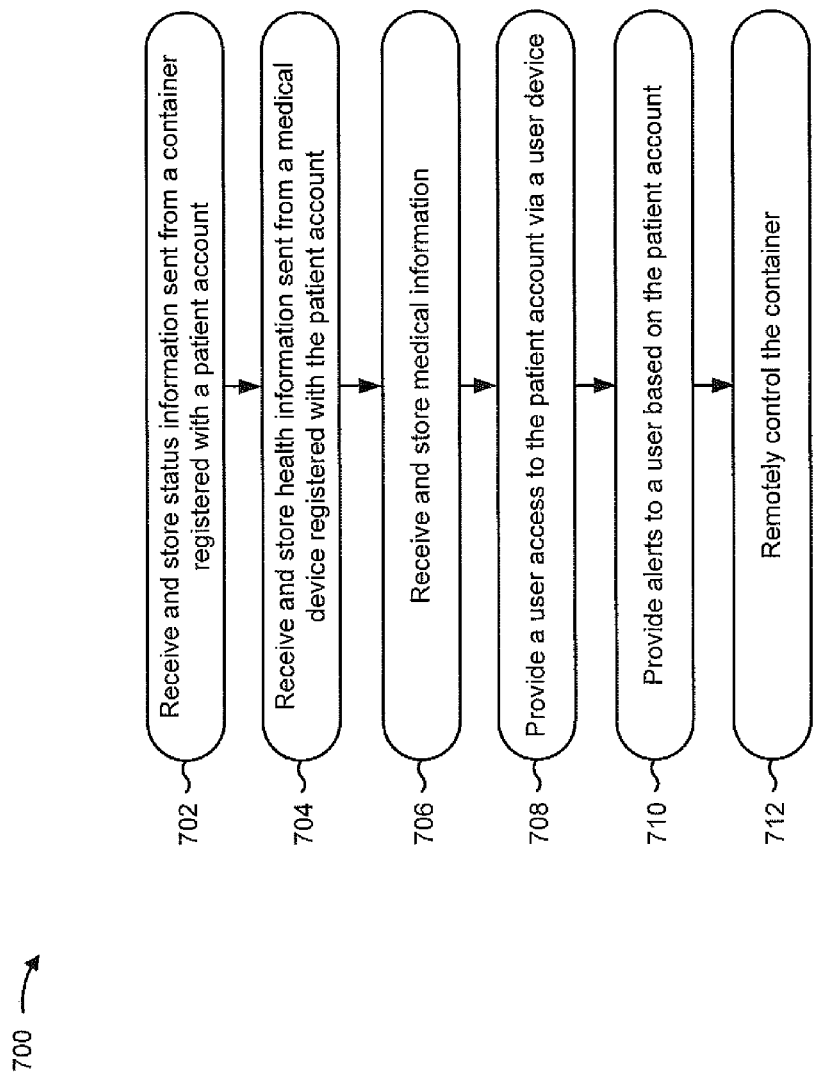
FIG. 7 is a flow chart of an example process for providing a service for monitoring patients.

FIG. 7 is a flow chart of an example process 700 for providing a service for monitoring patients. In some implementations, one or more process blocks of FIG. 7 may be performed by server device 240. In some implementations, one or more process blocks of FIG. 7 may be performed by another device or a group of devices separate from or including server device 240, such as container 210, user device 220 and/or medical device 230.

As shown in FIG. 7, process 700 may include receiving and storing status information sent from container 210 registered with a patient account (block 702). For example, server device 240 may receive the status information sent by container 210 at block 630 of FIG. 6B. Server device 240 may store the status information in the entry for the patient account in the account data structure.

As further shown in FIG. 7, process 700 may include receiving and storing health information sent from medical device 230 registered with the patient account (block 704). For example, server device 240 may receive and store the health information from medical device 230. A user may log into the patient account and register medical device 230 with the patient account at any time.

Medical device 230 may use a sensor to sense information about the patient's health. The health information may include the information about the patient's health. For example, the health information may indicate a heart rate, a blood pressure, a blood alcohol level, a blood glucose level, a breathing rate, a weight, a temperature, etc. In some implementations, server device 240 may instruct medical device 230 to sense the information about the patient's health at particular times and medical device 230 may sense the information about the patient's health at the instructed times. For example, server device 240 may instruct medical device 230 to sense the information at times that correspond to a dispense time that the patient is supposed to take the medication and/or times used to monitor the patient for possible side effects of taking the medication.

Medical device 230 may send the health information to server device 240 and server device 240 may receive the health information. Server device 240 may store the health information in the entry for the patient account in the account data structure.

As further shown in FIG. 7, process 700 may include receiving and storing medical information (block 706). For example, server device 240 may receive and store the medical information.

The medical information may include information about medications. For example, the medical information may indicate drug and food interactions with one or more medications the patient is taking. Additionally, or alternatively, the medical information may identify and alternative medication (e.g., a generic drug) that may be taken instead of a medication that the patient is taking. Furthermore, the medical information may identify the cost of medications and/or known side effects of medications. In some implementations, the medical information may include information about medical conditions (e.g., illnesses, diseases, etc.).

A device in environment 200 (e.g., user device 220) may send the medical information to server device 240 and server device 240 may receive the medical information. Server device 240 may store the medical information in a memory included in server device 240 and/or a memory accessible to server device 240.

As further shown in FIG. 7, process 700 may include providing a user access to the patient account via a user device (block 708). For example, server device 240 may provide an application (e.g., a web application and/or mobile application) and/or a website that a user (e.g., a patient, a family member, a caregiver, and/or a healthcare professional) may log into via user device 220 and access the patient account.

Server device 240 may provide the status information, the health information, the medical information, and/or the prescription information to the user via the application. For example, server device 240 may provide historical records of all past medications and/or health conditions to the user. Server device 240 may chart a history of the times, dates, and/or quantities of medications that were taken against patient vital statistics (e.g., health information) to correlate activities to health conditions.

In some implementations, server device 240 may provide information indicating times and dates the patient took the medication (e.g., when the medication was dispensed from container 210). Additionally, or alternatively, server device 240 may provide information indicating an amount of the medication that the patient dispensed each time and/or when the patient missed a time to take the medication. Accordingly, a user may monitor whether a patient is taking medication timely and as prescribed.

Additionally, or alternatively, server device 240 may provide information about how much medication remains in container 210. Accordingly, a user may monitor whether a patient needs the prescription refilled and/or if the patient needs a new prescription if there are no more refills remaining. Moreover, server device 240 may automatically request a refill and/or a new prescription from a pharmacy.

In some implementations, information relating to the patient's heart rate, blood pressure, blood alcohol level, blood glucose level, breathing rate, weight, temperature, or the like that are tracked over time may be provided to the user. Accordingly, a user may monitor an effect that the medication may be having on the patient's health and/or any changes in health that may affect the prescription.

Additionally, or alternatively, the patient account may identify milestones (e.g., events) that may be monitored by a user. For example, a milestone may include a certain amount of time since the patient started taking the medication and/or a change in the patient's health. Server device 240 may provide information indicating when a milestone has been reached so that a user (e.g., a patient and/or a healthcare professional) can determine whether to continue and/or alter the medication being taken by the patient. For example, the health information may indicate the patient is suffering from a threshold level of side effects and/or complications which may prompt a change in the medication being taken by the patient. Additionally, or alternatively, the health information may indicate the patient's health has improved to an extent where the medication should be changed or discontinued.

Providing a user access to the patient account via the application or website may allow the user to input comments or feedback to the patient account that may be viewed by other users. For example, a user may execute the application on user device 220 to input comments and user device 220 may send the comments to server device 240. Server device 240 may receive the comments and make the comments accessible to other users via the patient account. For example, a patient may input comments about how the patient is feeling, how the patient is sleeping, and/or if the patient is experiencing any problems with the medication. A healthcare professional may read the patient's comments and use the patient's comments to help treat the patient. As another example, a healthcare professional may input comments including instructions for the patient. Additionally, or alternatively, a patient may input comments or feedback directly into container 210 using an input component (e.g., a button(s), a touch screen, etc.). Container 210 may send the comments or feedback to server device 240 and server device 240 make the comments or feedback accessible to other users.

In some implementations, the application provided by server device 240 may allow users to communicate with other users associated with other patient accounts. For example, patients with similar illnesses and/or taking similar medications may communicate with each other. The application may also provide other enhancements to make it more likely a user will use the application. For example, the application may provide a calendar function allowing the user to schedule appointments or view community events, a weather function allowing the user to track the weather, a news function that provides news, and/or a social media function allowing the user to communicate socially with other users.

As shown in FIG. 7, process 700 may include providing alerts to a user based on the patient account (block 710). For example, server device 240 may provide alerts to users.

Server device 240 may provide an alert to a user using contact information associated with the user (e.g., a phone number, an email address, etc.). For example, server device 240 may provide an alert to the patient, a family member, a caregiver, and/or a healthcare professional. Moreover, server device 240 may provide alerts to container 210, user device 220, and/or medical device 230 (e.g., a device worn by the patient).

In some implementations, server device 240 may determine there is an emergency situation and send an alert to a user. For example, the health information may indicate the patient's blood pressure is dangerously high and requires immediate attention. Additionally, or alternatively, server device 240 may detect that the patient is prescribed medications that are known to have dangerous interactions. In some implementations, server device 240 may send an alert to emergency services (e.g., police department, fire department, hospital, etc.), container 210, user device 220, and/or medical device 230.

In some implementations, server device 240 may determine the patient has taken an inappropriate amount of the medication (e.g., the patient missed too many doses of a medication and/or taken too many doses of a medication) and send an alert. Additionally, or alternatively, server device 240 may send an alert to a user notifying the user that another user has input a comment to the patient account. In some implementations, server device 240 may send the comment to container 210 for display.

As further shown in FIG. 7, process 700 may include remotely controlling container 210 (block 712). For example, server device 240 may remotely control container 210.

In some implementations, server device 240 may send a command to container 210 to lock a lockable lid and not allow the lockable lid to be unlocked. For example, this may be necessary if container 210 is reported stolen and/or if it is determined that the patient is abusing the medication.

On the other hand, server device 240 may send a command to container 210 to unlock the lockable lid. For example, remote unlocking may be necessary if the biometric sensor breaks and the patient needs access to the medication. Additionally, or alternatively, remote unlocking may be necessary if there is an emergency situation that requires an unauthorized person to access the medication to give to the patient. Additionally, or alternatively, container 210 may be programmed to include a release mechanism that is triggered by an input of a specific sequence of buttons included in container 210. For example, emergency personal (e.g., 911 operators, emergency medical technicians (EMTs), medical professionals, etc.) may be provided with the specific sequence of buttons to unlock the lockable lid.

In some implementations, server device 240 may send a command to container 210 to emit a sound through a speaker, flash a light, and/or to activate a GPS if container 210 is lost and/or stolen. Server device 240 may track container 210 using the GPS and provide the location of container 210 to a user via the application.

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

Figure 8A:
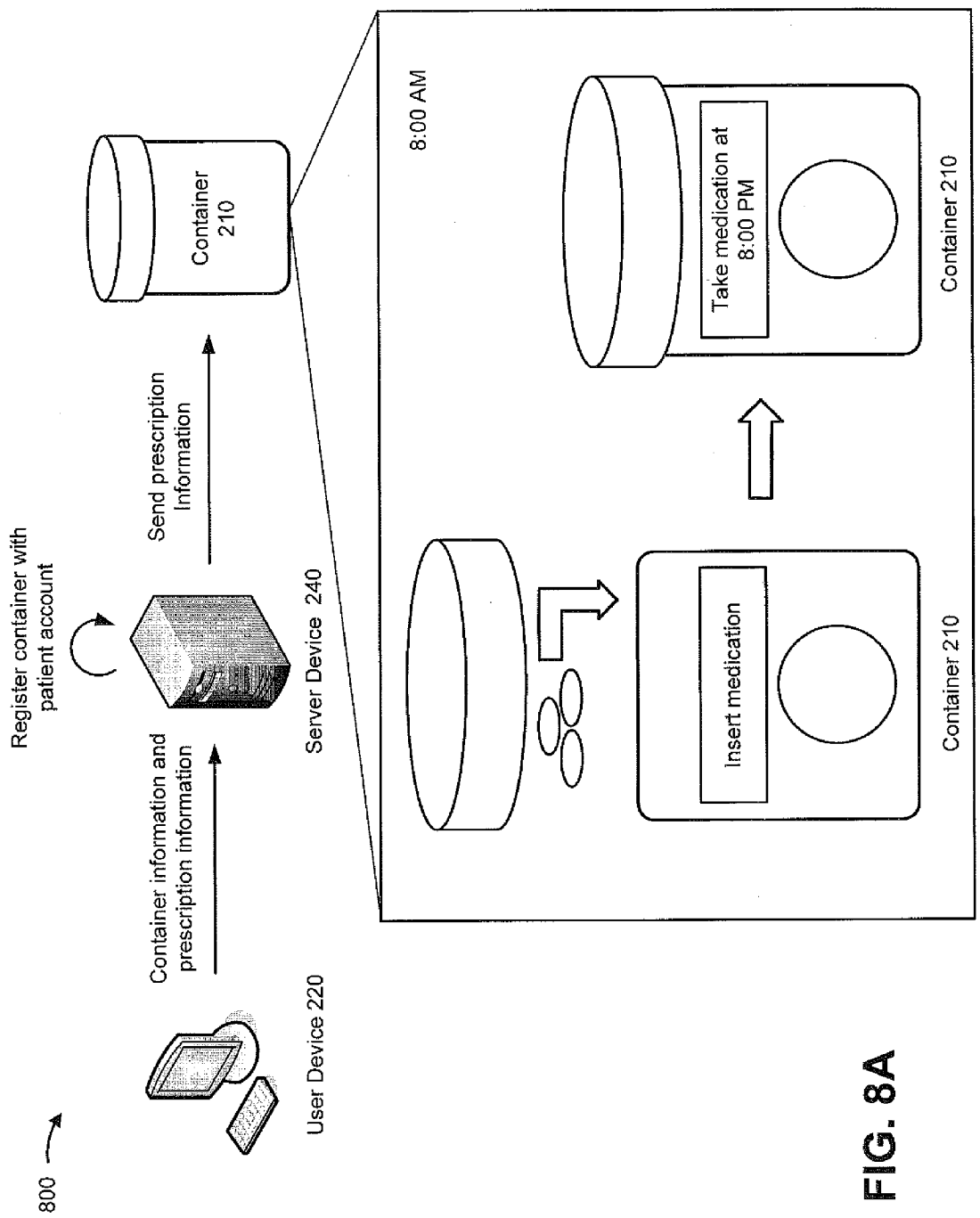
FIGS. 8A and 8B are diagrams of an example implementation relating to the example processes shown in FIGS. 5-7.
Figure 8B:
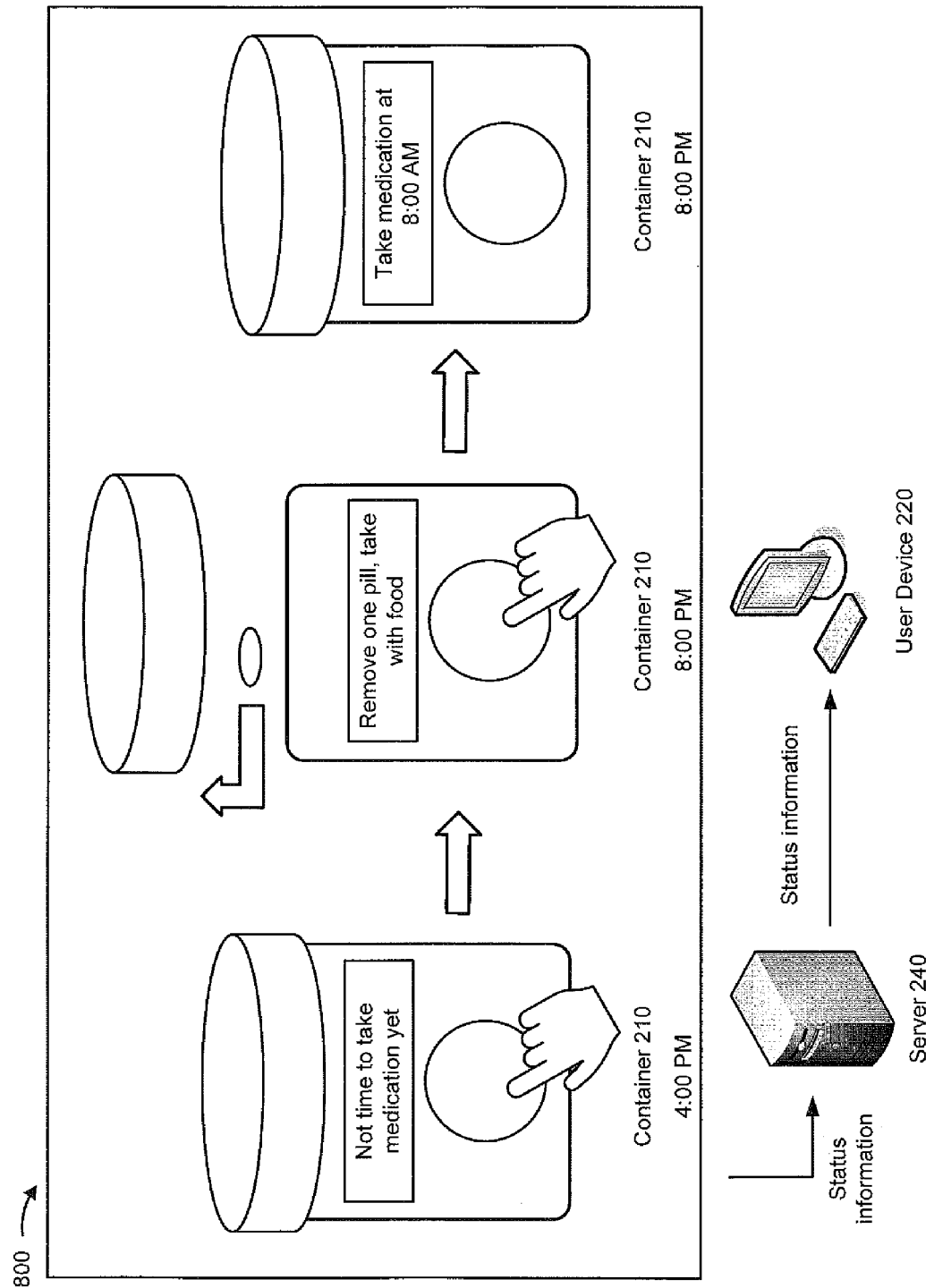

FIGS. 8A and 8B are diagrams of an example implementation 800 relating to example processes 500-700 shown in FIGS. 5-7. FIGS. 8A and 8B show an example of preparing container 210 to receive medication, providing access to medication held by container 210, and providing a service for monitoring patients.

In example implementation 800, assume server device 240 stores information in a patient account for a patient. Further, assume the patient has received medication the patient desires to be held by container 210. Also, assume the patient inputs container information identifying container 210 and prescription information identifying a prescription for the medication into user device 220. Assume the prescription information indicates that one pill should be taken every 12 hours with food.

As shown in FIG. 8A, user device 220 may send the container information, the prescription information, and a request to register container 210 with the patient account to server device 240. Server device 240 may receive the container information, the prescription information, and the request. Server device 240 may register container 210 with the patient account based on the request and the container information. Server device 240 may store the prescription information in connection with the patient account, and send the prescription information to container 210.

Container 210 may receive the prescription information and prompt the patient to insert the medication (e.g., pills) into container 210. For example, a display included in container 210 may display a message "insert medication." Assume the patient inserts the medication into container 210. In some implementations, container 210 may include a scale that weighs the medication. Container 210 may prompt the patient to input how many pills were inserted and the user may use buttons included in container 210 to input a number of pills inserted into container 210. Container 210 may use the scale to weigh the medication and determine a pill weight based on the weight of the medication and the number of pills inserted into container 210.

Assume the user closes a lockable lid included in container 210 at 8:00 AM. Container 210 may send a signal to the lockable lid causing the lockable lid to lock, thereby preventing access to the medication. Furthermore, container 210 may determine that a dispense time to dispense the medication is at 8:00 PM (i.e., 12 hours later) based on the prescription information. The display may display a message reminding the patient of the next dispense time. For example, the display may display a message "take medication at 8:00 PM."

As shown in FIG. 8B, the patient may try to unlock the lockable lid at 4:00 PM by touching a finger to a biometric sensor (e.g., a fingerprint scanner) included in container 210. Container 210 may determine that the lockable lid may not be unlocked at this time because the next dispense time is not until 8:00 PM. Container 210 may keep the lockable lid locked and display a message indicating a reason why the lockable lid was not unlocked and/or reminding the patient of the next dispense time. For example, the display may display a message "not time to take medication yet." Container 210 may send status information about the failed attempt to unlock the lockable lid to server device 240.

As further shown in FIG. 8B, container 210 may display a message at 8:00 PM instructing the patient to take the medication and instructions for taking the medication. For example, the display may display a message "remove one pill, take with food." The patient may touch the biometric sensor included in container 210. Container 210 may authenticate the patient is authorized to unlock the lockable lid based on a fingerprint sensed by the biometric sensor. Container 210 may also determine that if the present time matches a dispense time, the lockable lid may be unlocked. Accordingly, container 210 may weigh the medication using the scale and container 210 may unlock the lockable lid. Assume the patient opens the lockable lid, removes one pill from container 210, and closes the lockable lid. Container 210 may lock the lockable lid and weigh the medication again. Container 210 may determine that one pill was removed based on a change in weight of the medication matching a pill weight. Container 210 may display another message reminding the patient of the next dispense time. For example, the display may display a message "take medication at 8:00 AM." Container 210 may send status information to server device 240 indicating that one pill was removed at 8:00 PM by the patient (as identified by the patient's fingerprint).

Server device 240 may receive the status information and store the status information with the patient account. Server device 240 may make the patient account available to users via an application (e.g., a website, a mobile application, etc.). A user (e.g., the patient, a family member, a caregiver, a healthcare professional, etc.) may use user device 220 to access the patient account via the application. For example, server device 240 may send the status information about the failed attempt to remove a pill at 4:00 PM and the status information about the pill that was removed at 8:00 PM to user device 220. In this way, users may be provided with information about whether the patient is taking the medication as prescribed.

As indicated above, FIGS. 8A and 8B are provided merely as an example. Other examples are possible and may differ from what was described with regard to FIGS. 8A and 8B.

Implementations described herein may reduce intentional or unintentional abuse of medication by a patient. Also, implementations described here may make it easier for a patient to manage multiple medications with various dosing instructions than using traditional prescription bottles, and/or to avoid dangerous mixes of medications. Furthermore, implementations described herein may allow users to track the effects of medications on a patient and to ensure a patient is taking medication as prescribed. Moreover, implementations described herein may help reduce the risk of insurance fraud by ensuring unauthorized people do not have access to medications in the container. Additionally, implementations described herein may assist law enforcement (e.g., by locating stolen containers) and/or increase public safety (e.g., by automatically contacting emergency services when necessary).

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Certain user interfaces have been described herein and/or shown in the figures. A user interface may include a graphical user interface, a non-graphical user interface, a text-based user interface, etc. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

To the extent the aforementioned implementations collect, store, or employ personal information provided by individuals, it should be understood that such information shall be used in accordance with all applicable laws concerning protection of personal information. Additionally, the collection, storage, and use of such information may be subject to consent of the individual to such activity, for example, through "opt-in" or "opt-out" processes as may be appropriate for the situation and type of information. Storage and use of personal information may be in an appropriately secure manner reflective of the type of information, for example, through various encryption and anonymization techniques for particularly sensitive information.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items, and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A container, comprising:
   a chamber to hold a medication;
   a lockable lid that covers an opening of the chamber;
   a biometric sensor;
   a scale; and
   one or more processors to:
      store prescription information,
         the prescription information including how often the medication should be provided;
      measure a weight of the medication held by the chamber using the scale;
      receive biometric information sensed by the biometric sensor,
         the biometric information indicating a biometric feature of a person attempting to open the container;
      determine a dispense time based on the prescription information and a previous dispense time,
         the dispense time being associated with a time during which the person is scheduled to take the medication;
      calculate a range of time, during which the lockable lid is permitted to be unlocked, based on the dispense time;
      selectively unlock the lockable lid or keep the lockable lid locked,
         the lockable lid being unlocked based on:
            the biometric information being associated with an authorized user of the container, and
            a present time being within the range of time during which the lockable lid is permitted to be unlocked, and
         the lockable lid being kept locked based on the present time being outside of the range of time during which the lockable lid is permitted to be unlocked;
      generate status information,
         the status information including:
            an indication of the authorized user that unlocked the lockable lid, and
            an indication of a time at which the lockable lid of the container is unlocked; and
      provide the status information to a server device.

2. The container of claim 1, further comprising:
   a display device;
   where the prescription information further includes at least one of:
      a name of the medication,
      a concentration of the medication,
      an original quantity of medication for a prescription,
      a dosing instruction for the medication, or
      an interaction with the medication;
   where the dispense time includes a time at which the lockable lid is permitted to be unlocked based on a change in the weight of the medication and the prescription information; and
   where the one or more processors are further to:
      provide, for display on the display device, information indicating the dispense time and at least one of:
         information indicating the name of the medication,
         the concentration of the medication, the original quantity of medication for the prescription,
the dosing instruction for the medication, or
the interaction with the medication.

3. The container of claim 2, where the one or more processors are further to:
determine that none of the medication has been removed from the chamber at the dispense time; and
provide for display of a reminder to take the medication.

4. The container of claim 1, where the one or more processors are further to:
receive the prescription information,
the prescription information being input by a user via an input device of the container, and
the prescription information further including a preferred dosing time, and
where the one or more processors, when calculating the range of time during which the lockable lid is permitted to be unlocked, are to:
calculate the range of time during which the lockable lid is permitted to be unlocked based on a past time at which the lockable lid was unlocked, and the preferred dosing time.

5. The container of claim 1, where the one or more processors are further to:
determine a change in the weight of the medication based on a portion of the medication being removed from the chamber; and
determine a quantity of doses of medication removed from the chamber based on the change in weight and a dosage weight,
the dosage weight being a weight of a dose of the medication; and
where the one or more processors, when providing the status information to the server device, are to:
provide information identifying the quantity of doses of medication removed from the chamber to the server device.

6. The container of claim 1, where the one or more processors are further to:
receive information indicating a first quantity of doses of the medication held by the chamber;
determine a dosage weight of a dose of the medication based on the first quantity of doses of the medication and the weight of the medication; and
determine a second quantity of doses of medication removed from the chamber based on a change in weight of the medication and the dosage weight; and
where the one or more processors, when providing the status information to the server device, are to:
provide information identifying the second quantity of doses of medication removed from the chamber to the server device.

7. The container of claim 1, where the one or more processors, when providing the status information to the server device, are to:
provide information identifying a geographic location of the container to the server device.

8. A computer-readable medium storing instructions, the instructions comprising:
one or more instructions that, when executed by one or more processors, cause the one or more processors to:
store prescription information including how often a medication held by a container should be provided;
measure a weight of the medication held by the container;
receive biometric information associated with a person attempting to open the container;
determine a dispense time based on the prescription information,
the dispense time being associated with a time during which the person is scheduled to take the medication;
calculate a range of time, during which a lid of the container is permitted to be unlocked, based on the dispense time; and
selectively unlock the lid to allow the person to access the medication or keep the lid locked,
the lid being unlocked based on:
a present time being within the range of time during which the lid is permitted to be unlocked, and
the biometric information,
the lid being kept locked based on the present time being outside of the range of time during which the lid is permitted to be unlocked.

9. The computer-readable medium of claim 8, where the one or more instructions, when executed by the one or more processors, further cause the one or more processors to:
generate status information indicating a time at which the lid of the container is unlocked and indicating a quantity of medication removed from the container while the lid of the container is unlocked; and
provide the status information to a server device.

10. The computer-readable medium of claim 8, where the biometric information indicates at least one of a fingerprint, an eye pattern, a face pattern, or a vein pattern.

11. The computer-readable medium of claim 8, where the one or more instructions, when executed by the one or more processors, further cause the one or more processors to:
receive an input of the prescription information via an input device included in the container.

12. The computer-readable medium of claim 8, where the one or more instructions, when executed by the one or more processors, further cause the one or more processors to:
receive, from a server device communicatively connected to the container, an instruction to unlock the lid of the container; and
unlock the lid of the container based on the instruction from the server device.

13. The computer-readable medium of claim 8, where the one or more instructions, when executed by the one or more processors, further cause the one or more processors to:
determine an orientation of the container; and
measure the weight of the medication based on the orientation of the container.

14. A method, comprising:
storing, by one or more processors, prescription information including how often a medication held by a container should be provided;
measuring, by the one or more processors, a weight of the medication held by the container;
receiving, by the one or more processors, biometric information associated with a person attempting to open the container;
determining, by the one or more processors, a dispense time based on the prescription information and a previous dispense time,
the dispense time being associated with a preferred time during which the person is scheduled to take the medication;

calculating, by the one or more processors, a range of time, during which a lid of the container is permitted to be unlocked, based on the dispense time; and selectively unlocking, by the one or more processors, the lid to allow the person to access the medication or keeping, by the one or more processors, the lid locked, the lid being unlocked based on: the dispense time, the weight of the medication, the biometric information, and a present time being within the range of time during which the lid is permitted to be unlocked, and the lid being kept locked based on the present time being outside of the range of time during which the lid is permitted to be unlocked.

15. The method of claim 14, further comprising:
generating status information indicating a time at which the lid of the container is unlocked and indicating a quantity of medication removed from the container while the lid of the container is unlocked; and
providing the status information to a server device.

16. The method of claim 14, where the biometric information indicates at least one of:

a fingerprint,
an eye pattern,
a face pattern, or
a vein pattern.

17. The method of claim 14, further comprising:
receiving an input of the prescription information via an input device included in the container.

18. The method of claim 14, further comprising:
receiving, from a server device communicatively connected to the container, an instruction to unlock the lid of the container; and
unlocking the lid of the container based on the instruction from the server device.

19. The method of claim 14, further comprising:
determining an orientation of the container; and
measuring the weight of the medication based on the orientation of the container.

20. The container of claim 1, where the one or more processors are further to:
receive the prescription information from an application.

* * * * *